US010473550B2

(12) United States Patent
Li et al.

(10) Patent No.: US 10,473,550 B2
(45) Date of Patent: Nov. 12, 2019

(54) MULTI-LASER GAS LEAKAGE DETECTOR

(71) Applicant: Aurora Innovative Technology LLC, Missouri City, TX (US)

(72) Inventors: Jiebo Li, Pearland, TX (US); Xunmin Guo, Fulshear, TX (US); Wanyi Zhao, Missouri City, TX (US); Zhen Yin, Houston, TX (US); Chuhan Yuan, Sugarland, TX (US)

(73) Assignee: Aurora Innovative Technology LLC, Missouri City, TX (US)

( * ) Notice: Subject to any disclaimer, the term of this patent is extended or adjusted under 35 U.S.C. 154(b) by 0 days.

(21) Appl. No.: 16/024,304

(22) Filed: Jun. 29, 2018

(65) Prior Publication Data

US 2019/0003918 A1    Jan. 3, 2019

Related U.S. Application Data

(63) Continuation-in-part of application No. 15/678,052, filed on Aug. 15, 2017, now Pat. No. 10,113,956.
(Continued)

(51) Int. Cl.
*G01J 5/02* (2006.01)
*G01M 3/38* (2006.01)
(Continued)

(52) U.S. Cl.
CPC .............. *G01M 3/38* (2013.01); *G01M 3/00* (2013.01); *G01M 3/2807* (2013.01);
(Continued)

(58) Field of Classification Search
CPC ..... G01N 21/31; G01N 21/3504; G01N 21/39; G01N 33/0047; G01N 2021/1793;
(Continued)

(56) References Cited

U.S. PATENT DOCUMENTS 4,426,640 A * 1/1984 Becconsall ............ G01N 21/39
340/632
5,250,810 A * 10/1993 Geiger ............... G01N 21/3504
250/338.5
(Continued)

FOREIGN PATENT DOCUMENTS

JP       2003-294573     * 10/2003  ............. G01B 11/00

*Primary Examiner* — Kiho Kim
(74) *Attorney, Agent, or Firm* — Fenwick & West LLP

(57) ABSTRACT

A system remotely detects a gas leakage from a pipeline in an area. The system detects a gas leakage by determining an absorption or emission of gasses in the area. The gas detection system includes at least two light sources. The lasers can include lasers for detecting absorbance of gasses in the area, lasers for stimulating emission of gasses in the area, and lasers for detecting a pathlength. Absorption is determined based on the relative amplitude difference of emitted and reflected light beams. Emission is determined based on an amount emission stimulated by absorbed lasers. Pathlength is determined calculating time of flight of a light beam. The detection system calculates a concentration of the gasses in the area using the determined absorption and pathlength. The detection system can also generate an image representing a gas leakage in the area. The detection system may be attached to an unmanned aerial vehicle.

16 Claims, 7 Drawing Sheets

Related U.S. Application Data

(60) Provisional application No. 62/527,784, filed on Jun. 30, 2017.

(51) Int. Cl.
| | | |
|---|---|---|
| *G01N 21/35* | (2014.01) | |
| *G01M 3/00* | (2006.01) | |
| *G01N 33/00* | (2006.01) | |
| *G01N 21/3504* | (2014.01) | |
| *G01M 3/28* | (2006.01) | |
| *G01N 21/17* | (2006.01) | |
| *G01N 21/39* | (2006.01) | |

(52) U.S. Cl.
CPC ......... *G01N 21/35* (2013.01); *G01N 21/3504* (2013.01); *G01N 33/0027* (2013.01); *G01N 2021/1793* (2013.01); *G01N 2021/1795* (2013.01); *G01N 2021/3513* (2013.01); *G01N 2021/399* (2013.01)

(58) Field of Classification Search
CPC ..... G01N 2021/1797; G01N 2021/394; G01N 21/35; G01M 3/28; G01M 3/38; G01M 11/00; G01M 3/02
See application file for complete search history.

(56) References Cited

U.S. PATENT DOCUMENTS

| | | | | |
|---|---|---|---|---|
| 5,430,293 | A * | 7/1995 | Sato | G01M 3/38 250/330 |
| 7,075,653 | B1 * | 7/2006 | Rutherford | G01F 23/14 250/338.5 |
| 2005/0134859 | A1 * | 6/2005 | Kalayeh | G01N 21/31 356/437 |
| 2007/0040121 | A1 * | 2/2007 | Kalayeh | G01C 11/025 250/342 |
| 2015/0323449 | A1 * | 11/2015 | Jones | G01N 21/3103 356/437 |

* cited by examiner

MULTI-LASER GAS LEAKAGE DETECTOR

CROSS REFERENCE TO RELATED APPLICATIONS

This application is a continuation in part application of and claims the benefit of priority to U.S. application Ser. No. 15/678,052, filed Aug. 15, 2017, and also claims the benefit of priority to U.S. Provisional Application No. 62/527,784, filed Jun. 30, 2017, each of which is incorporated herein by reference in its entirety for all purposes.

BACKGROUND OF THE INVENTION

1. Field of the Invention

This description relates generally to detection of gas leakage, and more specifically detection of gas leakage using mid-infrared laser.

2. Description of the Related Art

Natural gas consumption in the U.S. is expected to increase rapidly. However, at the same time, gas delivery infrastructure is aging. Accordingly, reliable and timely detection of natural gas leakage is critical to ensure the gas delivery infrastructure's reliability. Conventional non-optical methods that detect natural gas leakage are based on various mechanisms such as manual inspection, acoustic monitoring; gas sampling; soil monitoring; flow monitoring; and software based dynamic modeling. However, these detection methods are often unreliable, inefficient, and expensive.

SUMMARY OF THE INVENTION

Described is a gas detection system for remotely detecting a gas leakage from a target in an area using multiple light beams. The gas detection system uses a mid-infrared (mid-IR) and/or a near infrared (near-IR) laser for detecting gas leakage. The gas detection system also calculates a concentration of the leaked gas in the area by determining an absorption of the mid-IR laser by the leaked gas and a pathlength of the near-IR laser. The gas detection system can generate a gas emission image that visually represents a gas leakage in the area.

To determine the absorption by the gas in the area, the gas detection system emits a light beam in the mid-IR wavelength range (2-10 micrometers) and observes the reflected light beam. In some embodiments, the mid-IR light beam continuously sweeps through a range of wavelengths. The mid-IR light beam may be modulated as it sweeps through the range of wavelengths. The gas detection system determines the pathlength by emitting another light beam in the near-IR wavelength range and observing the reflected light beam. The gas detection system can be attached to an unmanned aerial vehicle or other moving carrier.

BRIEF DESCRIPTION OF THE DRAWINGS

The invention has other advantages and features which will be more readily apparent from the following detailed description of the invention and the appended claims, when taken in conjunction with the accompanying drawings, in which:

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

Optical methods apply a light source (e.g., laser or "light beam") to illuminate target areas and measure light energy scattered and/or reflected by objects in the target areas. Received light is analyzed to detect substances of interest. The received light can indicate a substance because light having a particular wavelength is absorbed when passing through the leaked substances and/or light having a particular wavelength is emitted when the leaked substances lose absorbed energy. One disadvantage of this approach is that other substances that are not of interest can absorb light and thereby trigger false alarms.

I. System Configuration

Figure 1:
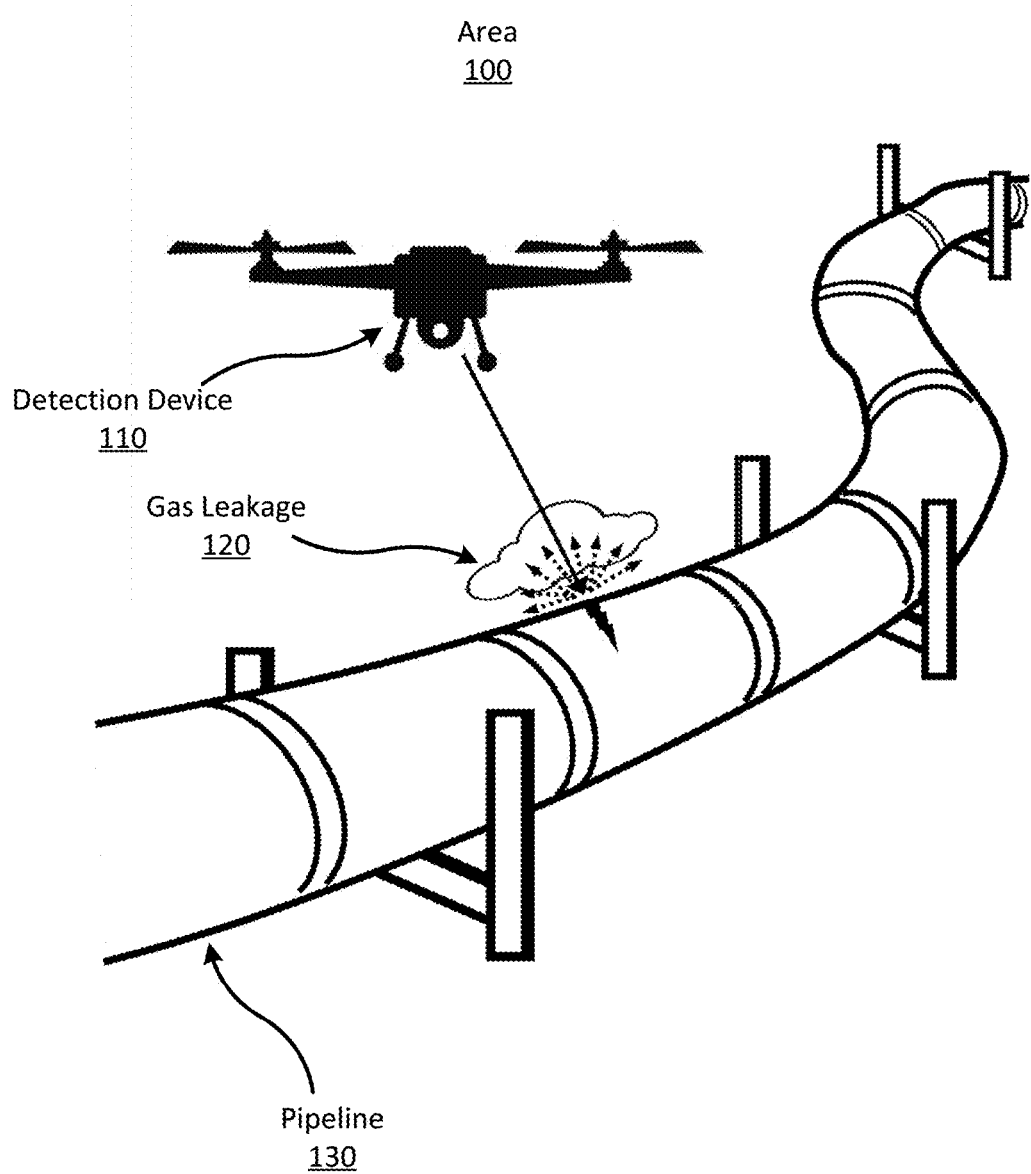
FIG. 1 illustrates an example area 100 in which an example gas detection system operates, according to one example embodiment.

FIG. 1 illustrates an example environment (e.g., area 100) in which an example remote gas-leakage detection device 110 ("detection device") operates. The detection device 110 detects a gas leakage 120 from a pipeline 130. The gas leakage 120 can include any number or combination of gases. The pipeline 130 can alternatively be any other conduit capable of transmitting gas(es). The detection device 110 includes at least two light sources (not shown) that emit light beams having the same or different wavelengths. The light sources illuminate the area 100 around the pipeline 130. The detection device 110 may calculate and/or measure an absorption rate of the light emitted by the light sources to determine a gas leakage 120 from the pipeline 130. Alternatively or additionally, the detection device 110 may calculate and/or measure an emission of the light absorbed by a gas to determine a gas leakage 120. The detection device can determine a type of gas in a gas leakage 120 based on the calculated absorption and emission. The detection device 110 can further measure a concentration of a gas in the gas leakage 120.

As illustrated in FIG. 1, the example detection device 110 includes a carrier such as an unmanned aerial vehicle. The detection device 110 operates in an area 100 near the pipeline 130 such as over the pipeline 130. The detection device 110 tracks the pipeline 130, for example, by flying in a route along the pipeline 130. Multiple detection devices can be deployed to detect a gas leakage 120 at different locations along the pipeline 130. Other embodiments are stand-alone gas-leakage detection devices that can be mounted to different carriers. For example, a remote-gas-leakage detection device can be attached to a balloon, a robot, an autonomous vehicle, and the like.

Figure 2:
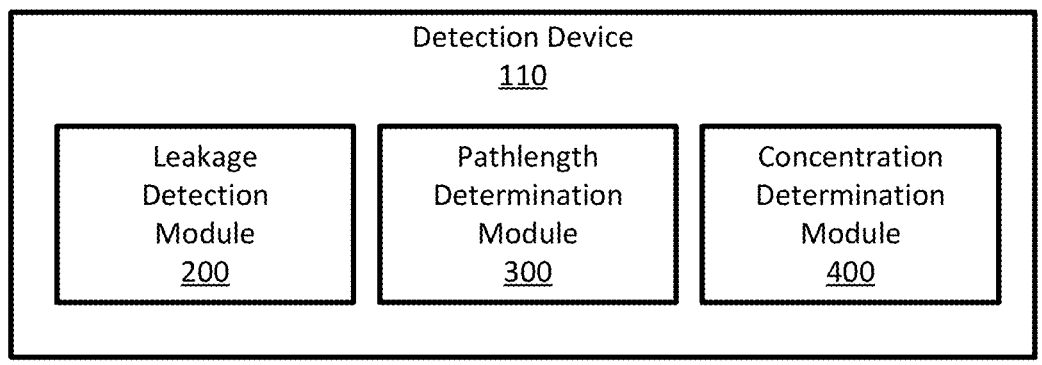
FIG. 2 illustrates a block diagram of an example gas detection device, according to one embodiment.

FIG. 2 illustrates an example detection device 110, according to one embodiment. The illustrated detection device 110 detects a gas leakage 120 by detecting the presence of one or more gases in an area 100 between the detection device 110 and a pipeline 130. The detection device 110 can additionally determine a concentration of the gas(es). The example detection device 110 includes a leakage detection module 200, a pathlength determination module 300, and a concertation determination module 400, all of which are further described below. As described herein, modules refers to hardware components, software components, and/or computational logic for providing functionality to gas detection systems. That is, a module can be implemented in hardware, mechanical elements, firmware, and/or software (e.g., a hardware server comprising computational logic), other embodiments can include additional modules, can distribute functionality between modules, can attribute functionality to more or fewer modules, can be implemented as a standalone program or as part of a network of programs, and can be loaded into memory executable by processors.

The leakage detection module 200 detects whether an area 100 includes a gas leakage 120. The leakage detection module 200 detects a gas leakage 120 by determining an absorption rate of a light beam or light beams by one or more gases in the area 100. Generally, the leakage detection module 200 emits a light beam in a direction towards a region of a pipeline 130 to be inspected. The emitted light beam traverses an area 100 towards a pipeline 130. An outer surface the pipeline 130 reflects the light beam emitted by the leakage detection module 200. The reflected light beam traverses the area 100 towards the detection device 110. If the pipeline 130 has a gas leakage 120, a gas leaks into the area 100 where the emitted light beam and the reflected light beam traverse. The gas absorbs some portion of the light beams according to the properties of the gas. By detecting absorption of light beams by a gas in the area 100, the leakage detection module 200 determines whether the region has a gas leakage 120.

The leakage detection module 200 can additionally or alternatively detect a gas leakage 120 by determining an emission of a gas in the area 100. For example, a gas in a gas leakage 120 may also emit additional light according to the properties of the gas. More explicitly, a gas in a gas leakage 120 is, generally, in an unexcited state. When light beams traversing the area 100 between the detection device 110 and the pipeline 130 are absorbed by the gas, the absorbed light excites the gas in the gas leakage 120 to an excited state. After a decay time, the gas in the excited state decays in energy from the excited state to the unexcited state and emits photons of a wavelength different from the absorbed light. By detecting the emitted light from the gas in the area 100, the leakage detection module determines whether there is a gas leakage 120.

A gas in a gas leakage 120 can be methane, ethane, ammonia, ethylene, propane, hydrocarbons, volatile organic compounds, or any other hazardous gas, etc. Section II describes various methods for determining a gas leakage including one or more gases using multiple light beams.

Figure 3A:
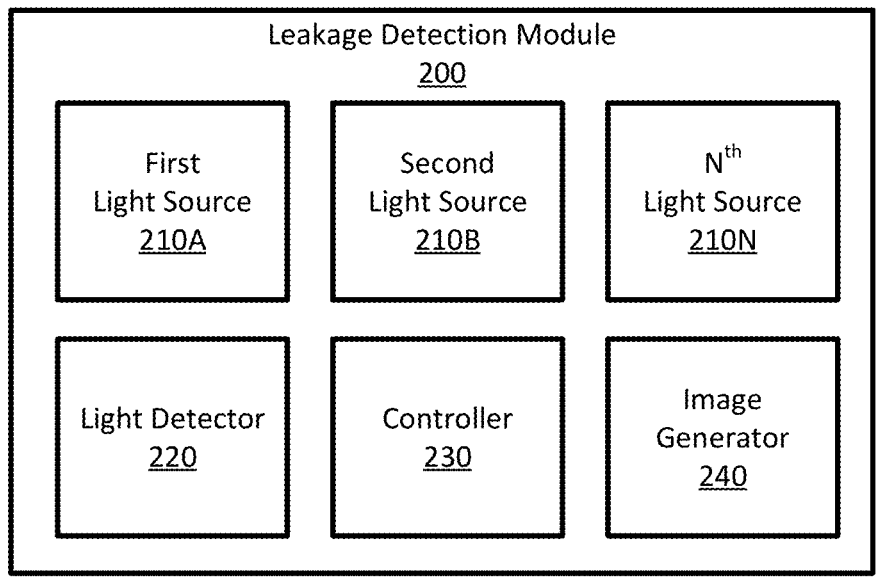
FIG. 3A illustrates a block diagram of an example leakage detection module, according to one example embodiment.

FIG. 3A illustrates a block diagram of a leakage detection module 200. The leakage detection module 200 includes a first light source 210A to emit a light beam having a first wavelength, a second light source 210B to emit a light beam having a second wavelength, a light detector 220 to detect light, a controller 230, and an image generator 240. As illustrated, the leakage detection module 200 also includes an $N^{th}$ light source 210N. The illustrated $N^{th}$ light source 210N indicates that a leakage detection module 200 can have 1, 2, . . . , N light sources 210 to emit light beams having a first, second, . . . , $n^{th}$ wavelength.

The controller 230 is coupled to the first 210A, second 210B, and $N^{th}$ 210N light sources. The controller 230 regulates any number of the light sources 210 to emit a light beam to illuminate a pipeline 130. In one example, the first light source 210A emits near-infrared (near-IR) light beam and the second light source 210B emits mid-infrared (mid-IR) light beam, but the emitted light beams may be any other wavelengths. The $N^{th}$ light source 210N may be any light source that emits a light beam from the near ultra-violet (near UV) to the mid-IR. The controller 230 can regulate the light sources 210 to emit light beams at predetermined intervals. Alternatively, the light sources 210 can be regulated to emit light beams continuously or substantially continuously. In some cases, one light source (e.g., 210A) can be regulated to emit a light beam continuously while another light source (e.g., 210B) is regulated to emit a light beam at a predetermined interval. Further, the controller 230 can regulate the light sources 210 to modulate the light beams in the time domain or frequency domain as described below.

The controller 230 is also coupled to a light detector 220. The light detector 220 can include a single or multiple sensors for detecting light (e.g., light beams, emitted light, etc.) having different wavelengths. The light detector 220 can be a single pixel or multi-pixel light detector such as a photodiode array. The light detector 220 can be any type of light detector such as a photoelectric detector, an infrared photodetector, a semiconductor photodetector, a photovoltaic photodetector, or any other photodetector that can measure the intensity of the collected light. For example, the photodetector is an HgCdTe detector or a PdSe detector. The light detector 220 captures incoming light and outputs electrical signals representing intensity of the captured light. The leakage detection module 200 analyzes the electrical signals generated by the light detector 220 to determine if there is a gas leakage 120 in an area 100.

The light detector 220 may additionally include collection optics, an optical filter, and/or an amplifier. The collection optics collect incoming light from the region of the gas pipe that is being inspected. The collection optics have a focus length such that the collected light are focused onto the light detector 220. In some embodiments, the collection optics include a Fresnel lens. The optical filter allows reflected light from the light beam emitted by the light source 210 to pass and removes other light collected by the collection optics that have wavelengths outside a particular range (e.g., mid-IR). Alternatively or additionally, the optical filter allows emitted light from a gas to pass and removes all other light collected by collection optics that have wavelengths outside a particular range. More generally, the optical filter removes ambient light (i.e., light that is undesirable for the detection of a gas leakage 120). The filtered light is directed towards a light detector 220. In cases where the light detector 220 includes an optical filter, only light of a certain wavelength generates electrical signals.

In one example embodiment, the optical filter includes a band-pass filter that allows light having wavelengths in the range of 3200-3300 nm to pass. In other examples, the band-pass filter can include any range of wavelengths between 2-10 ums (i.e., mid-IR range) to pass. In some embodiments, the wavelength range of the light removed by the optical filters can be configured and adjusted. The optical filer is coupled to the collection optics and the one or more light detectors 220. The optical filter can be a band pass filter, a notch filter, an optical high pass filter, an optical low pass filter, or any other type of optical filter. The amplifier is coupled to the one or more light detectors 220 and amplifies the output of the light detectors 220.

In various configurations, the detection device 110 can be configured such that light beams emitted by a light source 210 and collected by a light detector 220 are more easily analyzed by leakage detection module 200 to determine a gas leakage 120. For example, the detection device 110 may use the principle of tunable diode laser absorption spectroscopy (TDLAS). In these cases, the controller tunes a light source 210 to emit a light beam of a specific wavelength. The controller 230 can tune the wavelength by adjusting a temperature and/or an injection current density of the light source 210.

In some embodiments, the controller can regulate a light source 210 to emit a frequency modulated light beam. A wavelength of an emitted light beam can be modulated with a modulation signal at a higher frequency (e.g., a sinusoidal modulation signal at 10 kHz). The wavelength of the light beam can be associated with a particular gas in a gas leakage 120. The detection device 110 detects a harmonic (e.g., a first harmonic, a second harmonic) of the electrical signals generated by a light detector 220 that detects a reflected light beam. The detection device 110 analyzes the detected harmonic to determine the absorption rate. That is, the absorption intensity at a specific wavelength can be determined from the detected harmonic thereby to determine the absorption rate. The wavelength of the light source 210 may be continuously scanned across a range of wavelengths concurrently when the wavelength is modulated using the modulation signal. For example, the wavelength is continuously scanned from the wavelengths of 3245 nm to 3255 nm when the wavelength is modulated using the sinusoidal modulation signal at 10 k Hz. The leakage detection module 200 detects the absorption signal at the second harmonic of the modulation frequency which is at 20 kHz. The detected signal is analyzed to determine absorption rates of light at different wavelengths in the range of wavelengths (e.g., 3245-3255 nm).

The detection device 110 can also modulate different light beams at different frequencies. For example, the controller 230 can regulate the first light source 210A to emit a first light beam at a first wavelength using a modulation signal at a first frequency and regulate a second light source 210B to emit a light beam at a second wavelength using a modulation signal at a second frequency. Generally, the modulation signals are selected such that harmonics of for each modulation signal do not overlap. Additionally, the wavelength of each light beam can be selected such that it is absorbed by a particular gas in a gas leakage. For example, a detection device 110 emits two light beams with each light beam having a different wavelength and a different modulation signal. The detection device collects the reflected light beams after they have traversed the area 100 between the detection device 110 and the pipeline 130. Depending on the gases in a gas leakage 120 in the area 100, each light beam will be absorbed to varying degrees. The leakage detection module 200 can determine an absorption rate for various gases using the electrical signals generated by a light detector 220 that collects the light beams because the two beams are at different wavelengths and modulated at different frequencies. That is, the leakage detection module 200 analyzes the electrical signals obtained at a first modulation to determine the presence of a first gas that absorbs the first wavelength and, similarly, analyzes the electrical signals obtained at a second modulation to determine the presence of a second gas that absorbs the second wavelength. Accordingly, the detection device 110 can determine if a gas leakage includes different particular gasses. In various other embodiments, the detection device 110 can employ any other form of frequency modulation.

In some embodiments, a controller 230 can regulate various light sources 210 to emit light beams similarly to time division multiplexing. That is, using an example with two light beams, a controller 230 regulates a first light source (e.g., 210A) to emit a first light beam at a time $t_1$ with pulse width $w_1$. After a delay $d_1$, the controller 230 regulates a second light source (e.g., 210B) to emit a second light beam at a time $t_2$ with a pulse width $w_2$. After a delay $d_2$, the controller 230 again regulates the first light source to emit the first light beam. The controller 230 regulates the first and second light sources 210 to repetitively emit the first and second light beams one after the other. Each light source 210 can be configured to emit a light beam at any wavelengths and each wavelength can be associated with a particular gas in a gas leakage 120. In this example, the leakage detection module 200 de-multiplexes the electrical signals generated by a light detector 220 collecting reflected light beams. Because the two light beams are being emitted at specific times with a specific time pattern (i.e., widths and delays of the light beams), the each of the de-multiplexed electrical signals can be associated with a single light beam. Accordingly, the detection device 110 can determine if a gas leakage includes the particular gasses associated with the light beams. In other embodiments, the detection system may include more than two light sources generating more than two light beams with different widths and delays. Further, the detection device 110 can employ any other form of time domain modulation such as pulse width modulation or pulse position modulation to determine a gas leakage 120 in an area 100.

In some embodiments, the leakage detection module 200 can include an image generator 240. The image generator 240 generates a gas emission image of an area 100 around a pipeline 130. A gas emission image is a visual representation of the area 100 which includes information regarding the presence of a gas leakage 120 near the pipeline 130. In some cases, the image generator 240 generates a gas emission image using electrical signals produced by a light detector 220. In other cases, the image generator directly captures a gas emission image of the area 100. The image generator 240 can be coupled to a controller 230 such that the controller 230 regulates the image generator 240 to capture a gas emission image in an area 100 under inspection.

In some embodiments, the leakage detection module 200 analyzes information included in a gas emission image and detects a gas leakage 120. For example, a gas emission image includes pixels of which the pixel values (e.g., brightness levels) corresponds to presence of a gas leakage 120. Bright pixels in the image indicate the presence of a gas, while dark pixels in the image indicate the gas is not present. Accordingly, the leakage detection module 200 analyzes the pixel brightness values as well as a number of bright pixels to determine a gas leakage 120. For example, if a number of bright pixels in the image are above a threshold number, the leakage detection module 200 determines that there is a gas leakage 120. In various other examples, information that can indicate the presence of a gas leakage 120 in a gas emission image can include sharpness, contrast, color, brightness, shapes, etc. As such, the leakage detection module 200 can use any of the included information to determine a gas leakage from a gas emission image.

The image generator 240 can be configured to capture any range of wavelengths in a gas emission image. For example, the image generator 240 can be a thermographic camera that forms a gas emission image using infrared radiation. That is, the gas emission image is an infrared image of light in the wavelengths from 2400 to 12,000 nm in an area 100 around the pipeline 130. In other embodiments, the image generator is configured with an optical filter to capture an image for a range of wavelengths that correspond to the absorption or emission wavelengths of a particular gas. Because the image generator 240 can be configured to generate gas emission images using various wavelengths of light, the leakage detection module 200 can determine a gas leakage 120 for any gasses corresponding to wavelengths represented in the gas emission image.

Figure 3B:
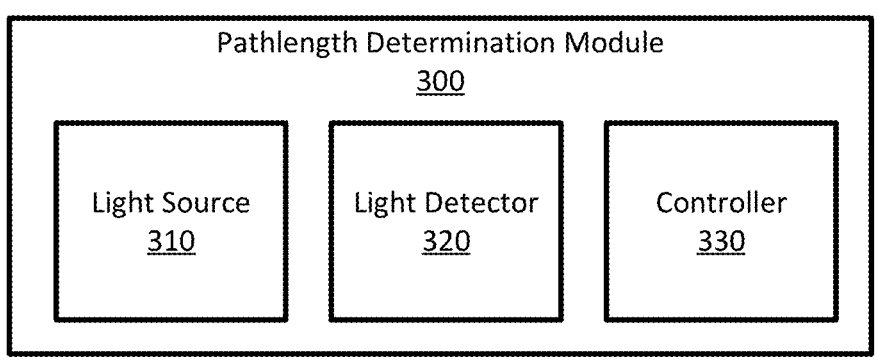
FIG. 3B illustrates a block diagram of a pathlength determination module, according to one example embodiment.

FIG. 3B illustrates an example pathlength detection module 300. The pathlength detection module 300 determines the pathlength of light beams emitted by light sources 210 of the detection device 110. The pathlength determination module 300 emits light beams towards the pipeline 130 and determines its pathlength. Because the light beams emitted by the pathlength determination module 300 and the light beams emitted by the leakage detection module 200 traverse substantially the same path, their pathlengths are substantially equal. The pathlength determination module includes a light source 310, a light detector 320, and a controller 330. The controller 330 is coupled to the light source 310 and the light detector 320. The light source 310, the light detector 320, and the controller 330 function similarly to the light source 210, light detector 220, and controller 230 the leakage detection module 200. As such, a description of these components are emitted herein.

In various embodiments, a light source 310 emits a light beam that is unlikely to be absorbed by a gas leakage 120 such that the pathlength can be more accurately determined. In some cases, the light beam is in the visible range (i.e., light having a wavelength in the range of 400-700 nm) or near infrared range (i.e., light having a wavelength in the range of 700 nm-1 μm). The controller 330 regulates the light source 310 to emit a light beam and regulates the light detector 320 to detect an incoming light beam that is the light beam emitted by the light source 310 being reflected by the pipeline 130.

In one example, the pathlength detection module 300 determines the pathlength by analyzing light beam characteristics of the collected light beam to determine the pathlength. In this case, the pathlength detection module 300 compares a phase of the collected light beam relative to that of the emitted light beam to determine a phase difference and, thereby, determine how long it takes the emitted light beam to traverse the light path. For example, the pathlength determination module 300 compares the temporal coherence between the emitted and the collected visible light beams.

In another example, the pathlength determination module 300 determines the pathlength by calculating the time of flight of a light beam. In this case, the controller 330 regulates the light source to emit a light beam towards a pipeline 130 at a first time $t_1$. The light beam is reflected off of the pipeline 130 and is collected by a light detector 320 at time $t_2$. The pathlength determination module 300 calculates the pathlength by calculating the difference in times $t_1$ and $t_2$, multiplying the difference by the speed of light, and dividing the result by two.

In various configurations, for an area 100 that is being inspected, the pathlength determination module 400 may calculate multiple pathlengths by emitting light beams towards the pipeline 130 along different directions. Each calculated pathlength may correspond to an absorption rate calculated by the leakage detection module 300.

The concentration determination module 400 calculates a concentration of a gas in a gas leakage 120. The concentration detection module 400 receives an absorption rate determined by the leakage detection module 200 and a pathlength determined by the pathlength determination module 300, and calculates the concentration of a gas in a gas leakage 120 according to equation (1):

$$A = \varepsilon \cdot L \cdot C \quad (1)$$

where A is the absorption rate of the light beam by a particular substance, E is the molar absorptivity of the substance, L is the pathlength of the light beam as it traverses the area 100, and C is the concentration of the substance. For a pipeline 130 that is being inspected, the concentration determination module 400 may calculate multiple concentration values corresponding to different locations of the pipeline 130. Each location corresponds to a direction of a light beam emitted by the leakage detection module 300. The detection device 110 outputs the determined concentration value to a user. The concentration determination module 400 may calculate the concentration if the leakage detection module 200 detects that there is a gas leakage 120. Alternatively, the concentration determination module 400 calculates the concentration concurrently with the leakage detection module 200 detecting whether there is a gas leakage 120. In some cases, the image generator 240 can use the determined concentration to generate a concentration image. The concentration image is a visual representation of a gas concentration in the area 100.

The detection device 110 may further include one or more other modules such as a locomotion module, a power module, an interface module, and a communication module. The locomotion module controls the movement of the detection device 110. The power module includes a battery pack and/or a protection circuit module as well as a power management system. Importantly, the power module powers the various components of the detection device 110 during operation. The interface module provides I/O functionality including user interfaces, data acquisition modules, USB interfaces, network interfaces, or any other input or output device that can be used to interact with and control the detection device 110. The communication module includes a wireless communication system that is based on various communication protocols such as long term evolution (LTE), 3G, 4G, and/or 5G mobile communication standards.

Compared to using near-IR light to detect gas leakage, embodiments described herein using mid-IR light to detect gas leakage more accurately, more reliably, more quickly, and with a higher sensitivity. Various embodiments described herein can detect leaked gas at a much lower concentration than conventional systems. For example, one embodiment can detect leaked methane in the order of 0.05 meter parts per million (ppm·m).

II. Determining a Gas Leakage Using Multiple Lasers

In various configurations, the detection device 110 can emit any number of light beams, collect the light beams, and determine if there is a gas leakage 120. By emitting light beams of differing wavelengths, the leakage detection module can determine various gasses included in a gas leakage 120. In particular, the wavelengths of the light sources 210 may be chosen such that absorption of the light, or emission of light, by a particular gas (or gasses) can be detected. For example, a first light source may be configured to emit a wavelength absorbed by methane, and a second light source may be configured to emit a wavelength absorbed by ethylene. The light sources 210 can be regulated to emit light concurrently or separately. The wavelength of the light beams can be tuned at startup of the detection device, remotely by an operator, or by accessing instructions stored on the system controller 230.

Figure 4A:
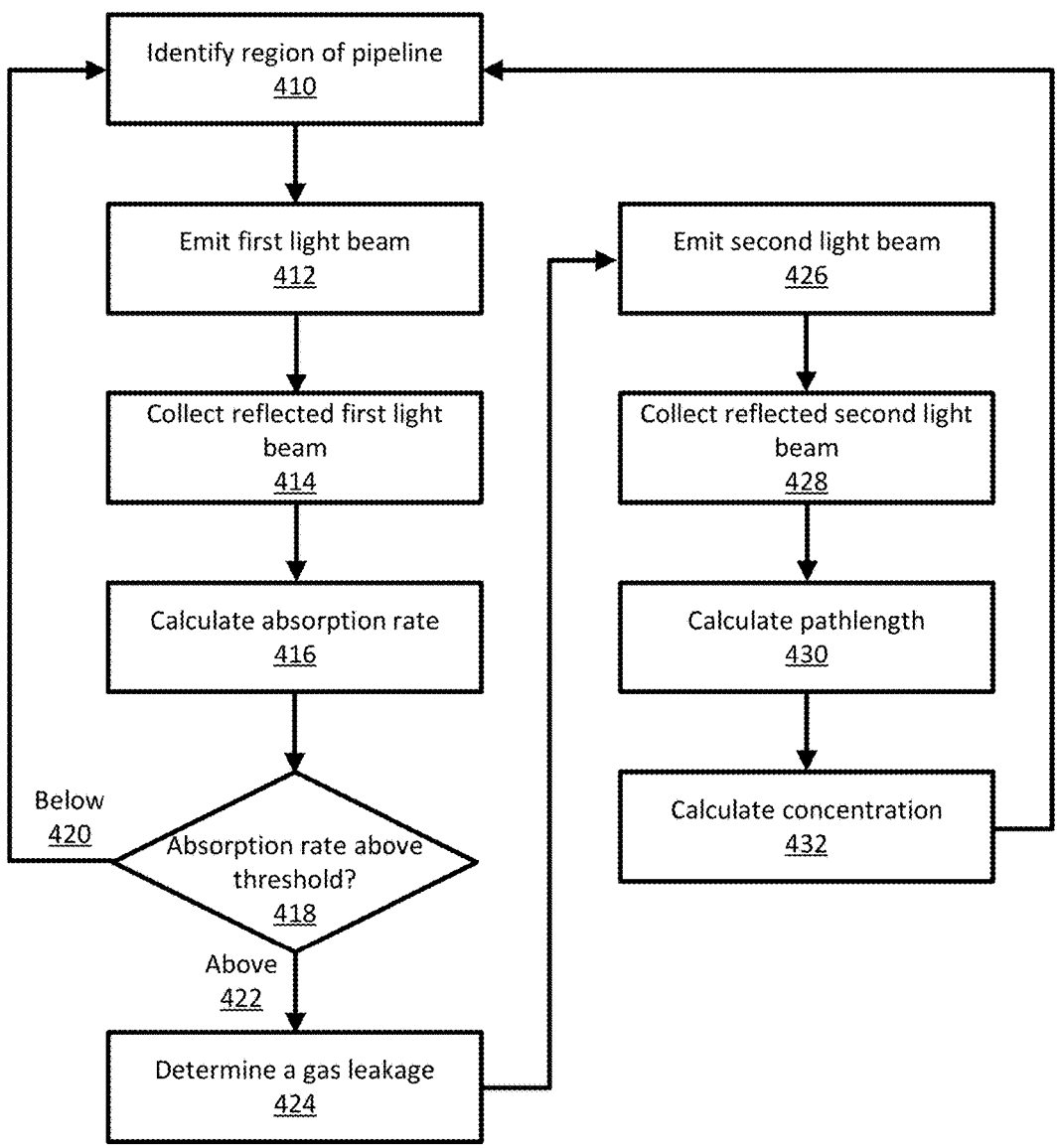
FIG. 4A-4C are flow charts illustrating example processes for detecting gas leakage with multiple light beams, according to one embodiment.
Figure 4B:
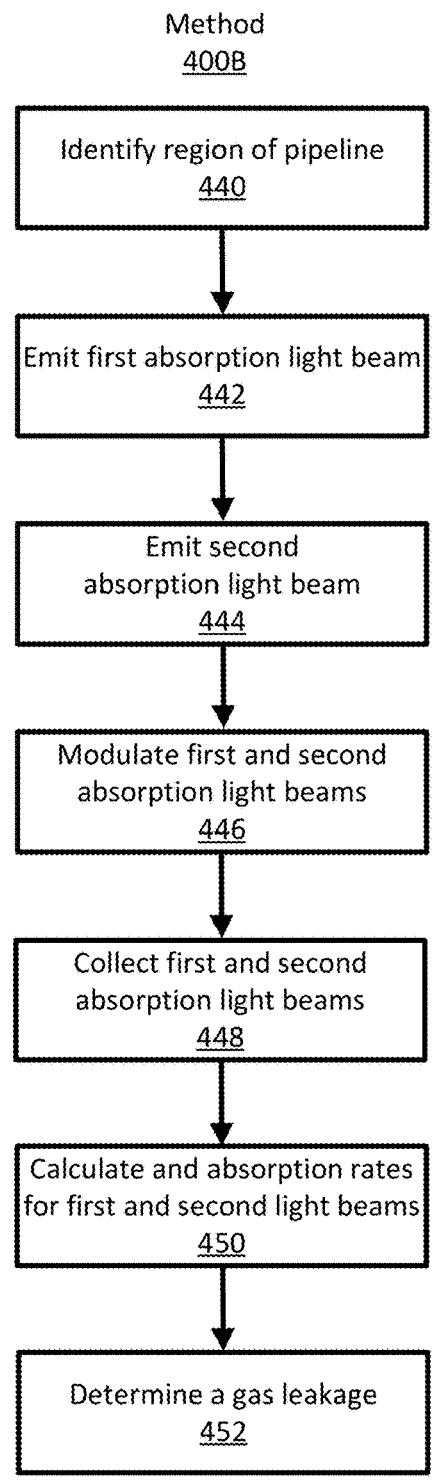
Figure 4C:
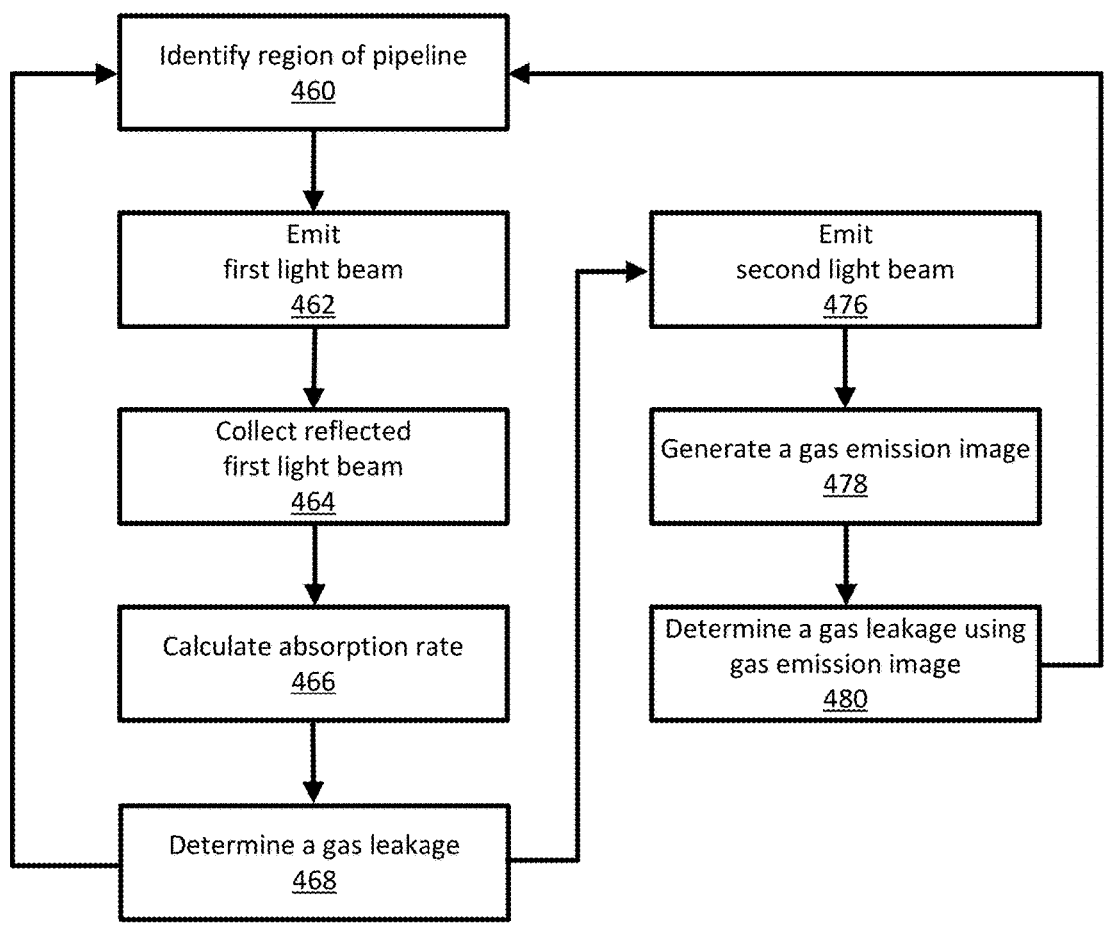

FIGS. 4A-4C are flow charts illustrating several example methods for detecting a gas leakage using multiple light beams using the methodologies described herein. The methods may include, but are not limited to, their constituent steps. Further, the methods are given by means of example of detecting a gas leakage using multiple emitted light beams. In various configurations, any combination of emitted light beams and methodologies may be used to detect a gas leakage, determine absorption rates, determine a concentration, and generate a gas emission image.

II.A First Example Method

FIG. 4A is a flow chart illustrating an example method 400A for detecting a gas leakage 120 using multiple light beams. The detection device 110 identifies 410 a region of a pipeline 130 in the area 100 to inspect for a gas leakage 120. The detection device 110 inspects a region of the pipeline at a particular time point as it traverses along the pipeline. A dimension of a region inspected at a time point can be predetermined by a user or determined by the detection device 110 according to the ambient environment. The regions are selected such that there is no gap between any two consecutive regions such that the detection device 110 can inspect the pipeline 130 entirely or substantially entirely within the area 100.

The detection device 110 emits 412 a first light beam towards the region of the pipeline 130. The first light beam has a wavelength that is in the mid-IR range. The wavelength can be predetermined or determined based on a gas that might be included in a gas leakage 120. In some embodiments, the detection device 110 emits multiple light beams along different directions towards the region either concurrently or sequentially. These light beams are incident on different locations of the pipeline in the area 100. This way, the detection device 110 can inspect the different regions of the pipeline within the area 100.

The detection device collects 414 a first reflected light beam which is the first light beam emitted by the detection device 110 and reflected off of an outer surface of the pipeline 130 being inspected.

The detection device calculates 416 an absorption rate of the first light beam by a gas in an area 100 between the detection device 110 and the region of the pipeline 130 being inspected using the emitted light beam and the collected light beam. For example, the detection device 110 compares an intensity of the emitted light beam to an intensity of the reflected light beam to calculate the absorption rate. In some embodiments, the detection device 110 calculates multiple absorption rates corresponding to the different regions of the pipeline 130.

The detection device 110 compares 418 the calculated absorption rate to a threshold absorption rate. If the calculated absorption rate is less than the threshold 420, the detection device identifies 410 a next region to be inspected. If the calculated absorption rate is above the threshold 422, the detection device 110 determines 424 that the region being inspected has a leakage 120.

Subsequently, the detection device emits 426 a second light beam towards the region that is being inspected. The second light beam has a second wavelength that is in the near-infrared range.

The detection device 110 collects 428 a second reflected light beam which is the second light beam emitted by the detection device 110 and reflected off of an outer surface of the pipeline 130 being inspected.

The detection device 110 calculates 430 a pathlength of the light beam using the emitted light beam and the collected light beam. For example, the detection device 110 determines the time of flight of the light beam (e.g., the time between emission and collection) to calculate the pathlength.

The detection device calculates 432 a concentration of a particular gas in the area 100 between the detection device 110 and the pipeline 130 using the determined absorption rate and pathlength. The detection device 110 transitions to identify 410 and inspect a next region. In some embodiments, the detection device 110 can emit multiple light beams along different directions towards the region of the pipeline 130 being inspected and calculates multiple pathlengths and/or concentrations along those different directions, either sequentially or concurrently.

In the illustrated example, the detection device 110 emits the second light beam to calculate the pathlength and the concentration if the detection device 110 determines 424 there is a gas leakage 120. In other embodiments, the detection device 110 emits the first and second beams concurrently and calculates the absorption rate and the pathlength. In further embodiments, the detection device 110 concurrently calculates the absorption rate, the pathlength, and the concentration.

II.B Second Example Method

FIG. 4B is a flow chart illustrating an example method 400B of detecting a gas leakage 120 using multiple light beams. The detection device 110 identifies 440 a region of a pipeline 130 to inspect for a gas leakage 120. Similar to method 400A, the detection device 110 selects dimension of the region such that there are no gap between any two consecutive regions such that as the detection device 110 traverses the pipeline 130.

The detection device 110 emits 442 a first light beam towards the region using a first light source. The first light beam has a first wavelength that is in the mid-IR range. The detection device 110 emits 444 a second light beam towards the region using a second light source. The second light beam has a second wavelength that is in the mid-IR range. The first and second wavelength can be predetermined or determined based on a particular gas that may be in a gas leakage 120.

The detection device 110 modulates 446 the first and second light beams. In one example, the first and second light beams are multiplexed such that, repeatedly, a first light source 210A emits the first light beam and then a second light source 210B emits the second light beam. In various examples, the light beams are multiplexed according to a timing pattern. The timing pattern includes the start times, pulse widths, and time delays for the multiplexed light beams. In another example, the detection device 110 frequency modulates the first light beam and the second light beam using different modulation signals. For example, the first light beam is modulated at a first frequency and the second beam is modulated at a second frequency. The frequencies are selected such that their harmonics are non-overlapping.

The detection device 110 collects 448 a first reflected light beam and a second reflected light beam which are the first light beam and second light beam emitted by the detection device 110 and reflected off of an outer surface of the pipeline 130 being inspected, respectively. In one example, the reflected light beams are collected using the same light detector 220.

The detection device 110 calculates 450 an absorption rate for two gasses in the region. The detection device 110 demodulates the electrical signals generated by collected light beams on the light detector 220 into electrical signals of the first reflected light beam and electrical signals of the second reflection light beam. The detection device 110 calculates the absorption rate of a first gas in the region using electrical signals representing the first emitted light beam and the electrical signals of the first reflected light beam. For example, the detection device 110 compares an intensity of the first emitted light beam to an intensity of the first reflected light beam to calculate the absorption rate. The detection device 110 calculates 450 an absorption rate by a second gas in the region using the second emitted light beam and electrical signals of the second reflected light beam in a similar manner.

The detection device 110 determines 452 a gas leakage based on the calculated absorption rates. For example, the detection device 110 compares the calculated absorption rates to threshold absorption rates. If the calculated absorption rates are less than the threshold, the detection device 110 selects a next region to be inspected. If a calculated absorption rate (or rates) is above the threshold, the detection device 110 determines that the region being inspected has a gas leakage 120.

The detection device 110 can subsequently calculate a concentration of gasses detected in a gas leakage 120 similarly to method 400A.

II.C Third Example

FIG. 4C is a flow chart illustrating an example method 400C of detecting a gas leakage 120 using multiple light beams. The detection device 110 identifies 460 a region of a pipeline 130 to inspect for a gas leakage 120. Similar to method 400A, the detection device 110 selects a dimension of the region such that there are no gap between any two consecutive regions such that as the detection device 110 traverses the pipeline 130.

The detection device 110 emits 462 a light beam towards the region of the pipeline 130. The light beam has a wavelength that is in the mid-IR range. The wavelength can be predetermined or determined based on a gas that might be included in a gas leakage 120. In some embodiments, the detection device 110 emits multiple light beams along different directions towards the region either concurrently or sequentially.

The detection device collects 464 a first reflected light beam which is the light beam emitted by the detection device 110 and reflected off of an outer surface of the pipeline 130 being inspected.

The detection device 110 determines 468 a gas leakage based on the calculated absorption rate. For example, the detection device 110 compares the calculated absorption rates to threshold absorption rates. If the calculated absorption rate is less than the threshold, the detection device 110 selects a next region to be inspected. If the calculated absorption rate is above the threshold, the detection device 110 determines that the region being inspected has a gas leakage.

Subsequently, the detection device emits 476 a second light beam towards the region that is being inspected. The second light beam has a second wavelength that is in the infrared range. The second wavelength corresponds to a wavelength will be absorbed by the gas in the detected gas such that the gas emits a third wavelength of light when the gas decays in energy. That is, the second light beam stimulates emission of photons at a third wavelength from the gas.

The detection device 110 generates 478 a gas emission image using an image generator 240. The image generator is configured with a bandpass filter corresponding to the third wavelength. Thus, the gas emission image is a visual representation of the inspected region highlighting showing where the third wavelength (i.e., the gas) is detected.

In some examples, the detection device 110 can determine a gas leakage 120 by analyzing the gas emission image. For example, the detection device may determine that there is a requisite number of bright pixels in the image to indicate a gas leakage. Further, the detection device determines that the bright pixels approximate the shape of a gas plume. Accordingly, the detection device determines that there is a gas leakage. In some embodiments, the detection device can store the gas detection image on a storage device if a gas leakage is determined. Alternatively or additionally, the detection device can transmit a gas detection image to a user remote from the detection device.

In the illustrated example, the detection device 110 emits the light beam to generate a gas emission image if the detection device 110 determines 468 there is a gas leakage 120. In other embodiments, the detection device 110 concurrently emits the first and second light beams and concurrently calculates the absorption rate and generates a gas emission image.

In some examples, the method 400C can generate a gas emission image representing multiple types of gas in a single image. In these cases any number of additional or alternative laser sources can generate light beams corresponding to the appropriate gasses. Alternatively, the image generator may be configured to generate images with various different interchangeable optical filters.

III. Unmanned Aerial Vehicle

Figure 5:
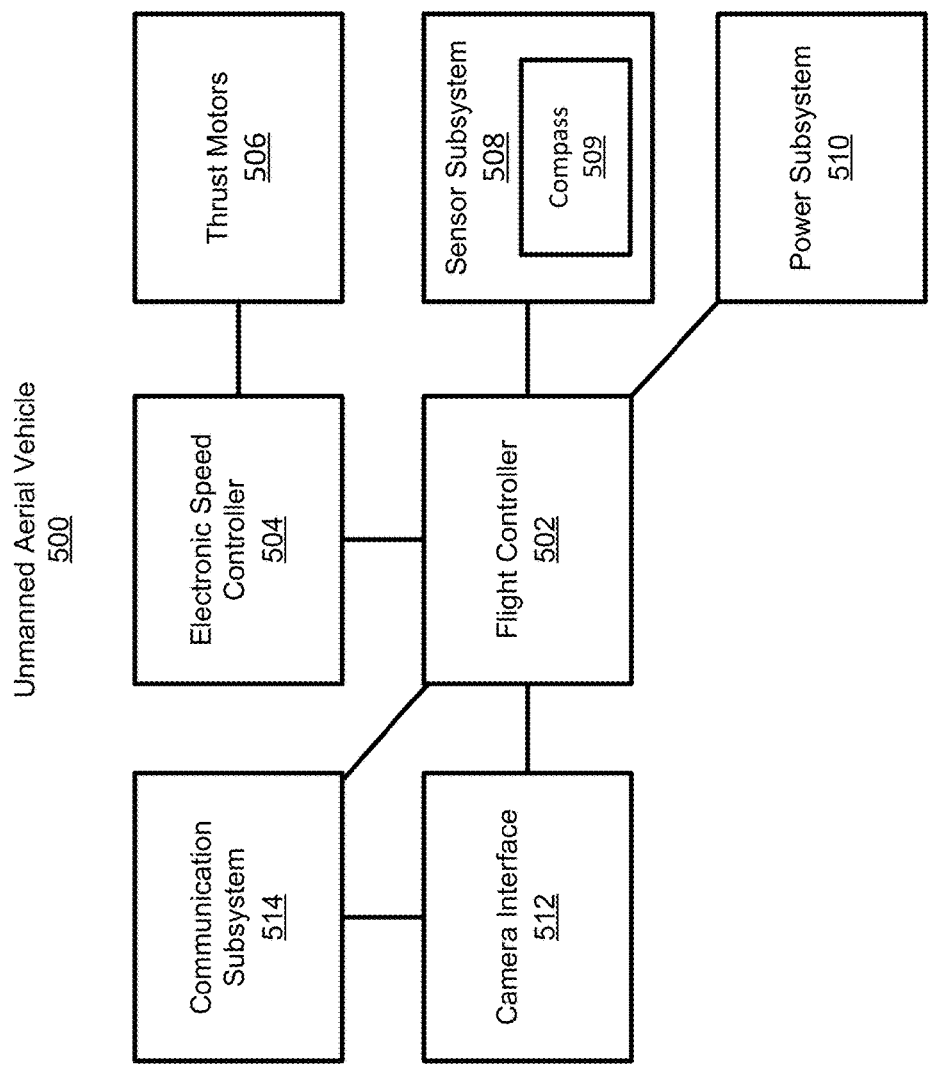
FIG. 5 illustrates a block diagram of an example unmanned aerial vehicle.

FIG. 5 illustrates a block diagram of an example unmanned aerial vehicle. The example unmanned aerial vehicle may be included in a detection device 110 or be separate from the gas detection device 110. The example UAV 500 includes a flight controller 502, an electronic speed controller 504, one or more thrust motors 506, a sensor (or telemetric) subsystem 508, a power subsystem 510, a camera interface 512, and a communication subsystem 514. The components may communicate directly or indirectly with each other through a data bus on the aerial vehicle 500.

The communication subsystem 514 may be a long-range Wi-Fi system. The communication subsystem 514 may include or be another wireless communication system, for example, one based on long term evolution (LTE), 3G, 4G, and/or 5G mobile communication standards. The communication subsystem 514 also may be configured with a unidirectional RC channel for communication of controls from a remote controller to the aerial vehicle 500 and a separate unidirectional channel for video downlink from the aerial vehicle 500 to the remote controller (or to a video receiver where direct video connection may be desired). The sensor subsystem 508 may include navigational components, for example, a gyroscope, accelerometer, a global positioning system (GPS) and/or a barometric sensor. The telemetric compass may also include an unmanned aerial vehicle (UAV) compass 509. The UAV compass 509 may include one or more magnetometer sensors with which it determines the orientation of the aerial vehicle 500. The power subsystem 510 may include a battery pack and/or a protection circuit module as well as a power control and/or battery management system. The camera interface 512 may interface with an image capture device or may include an integrated image capture device.

The flight controller 502 may communicate with a remote controller through the communication subsystem 516. The flight controller 502 controls the flight related operations of the aerial vehicle 500 by controlling the other components such as the electronic speed controller 504 and/or the sensor subsystem 508. The flight controller 502 can configure the flight path, the speed, the trajectory, and the position of the aerial vehicle 500 based on input from the user (for instance, via a remote controller). In addition, the flight controller 502 can configure the flight path, speed, trajectory, and position of the aerial vehicle 500 without receiving input from the user, for instance when the aerial vehicle 500 is adjacent to, within a threshold proximity of, or flying towards a virtual wall or NFZ.

The electronic speed controller 504 may be configured to interface with the thrust motors 506 (via an electronics interface) to control the speed and thrust applied to the propellers of the aerial vehicle 500. The flight controller can communicate with the camera interface 512 to capture and transmit images from an image capture device to the remote controller (or other device with a screen such as a smart phone), e.g., via the communication subsystem 514. The power subsystem 510 may be configured to manage and supply power each of the components of the aerial vehicle 500.

IV. Additional Considerations

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents.

In alternate embodiments, the invention is implemented in computer hardware, firmware, software, and/or combinations thereof. Apparatus of the invention can be implemented in a computer program product tangibly embodied in a machine-readable storage device for execution by a programmable processor; and method steps of the invention can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language or in assembly or machine language if desired; and in any case, the language can be a compiled or interpreted language.

Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits) and other forms of hardware.

The term "module" is not meant to be limited to a specific physical form. Depending on the specific application, modules can be implemented as hardware, firmware, software, and/or combinations of these. In the example gas leakage detection devices described above, the modules were implemented as software, typically running on digital signal processors or even general-purpose processors. In other applications, the modules can be implemented as dedicated circuitry (e.g., part of an ASIC), in order to take advantage of lower power consumption and higher speed. Various combinations can also be used. For example, certain operations, like the FFT, inverse FFT, application of a filter, sequence estimation and decoding, may be common enough as to be available as standard components, software, or circuit designs. These may be combined with customized implementations of the remainder of a gas leakage detection device. Furthermore, different modules can share common components or even be implemented by the same components. There may or may not be a clear boundary between different modules.

A gas leakage detection device can comprise multiple elements. An element may comprise any physical or logical structure arranged to perform certain operations. Each element may be implemented as hardware, software, or any combination thereof, as desired for a given set of design parameters or performance constraints. Examples of hardware elements may include devices, components, processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), memory units, logic gates, registers, semiconductor device, chips, microchips, chip sets, and so forth. Examples of software may include any software components, programs, applications, computer programs, application programs, system programs, machine programs, operating system software, middleware, firmware, software modules, routines, subroutines, functions, methods, interfaces, software interfaces, application program interfaces (API), instruction sets, computing code, computer code, code segments, computer code segments, words, values, symbols, or any combination thereof. Although the example gas leakage detection device as shown in FIG. 2 has a limited number of elements in a certain topology, it may be appreciated that other embodiments of a gas leakage detection device may include more or less elements in alternate topologies as desired for a given implementation. The embodiments are not limited in this context.

Depending on the form of the modules, the "coupling" between modules may also take different forms. Dedicated circuitry can be coupled to each other by hardwiring or by accessing a common register or memory location, for example. Software "coupling" can occur by any number of ways to pass information between software components (or between software and hardware, if that is the case). The term "coupling" or "coupled" is meant to include all of these and is not meant to be limited to a hardwired permanent connection between two components. In addition, there may be intervening elements. For example, when two elements are described as being coupled to each other, this does not imply that the elements are directly coupled to each other nor does it preclude the use of other elements between the two.

What is claimed is:

1. A system for remotely detecting gas leakage from a pipeline comprising:
    an image generator configured to capture images of light in a range of wavelengths;
    a first light source to emit a first outgoing light beam having a first wavelength and a second outgoing light beam having a second wavelength in a mid-infrared range, the first outgoing light beam and the second outgoing light beam traversing an area between the system and the pipeline towards a region of the pipeline, the first outgoing light beam modulated at a first modulation signal having a first frequency and the second outgoing light beam modulated at a second modulation signal having a second frequency different from the first frequency, and
    a light detector configured to detect a first incoming light beam having the first wavelength and a second incoming light beam having the second wavelength, the first incoming light beam being the first outgoing light beam reflected off of an outer surface of the region and the second incoming light beam being the second outgoing light beam reflected off of the outer surface of the region;
    a controller configured to:
        compare an intensity of the first incoming light beam to an intensity of the first outgoing beam to calculate a first absorption rate,
        compare an intensity of the second incoming light beam to an intensity of the second outgoing beam to calculate a second absorption rate,
        responsive to determining the first absorption rate above a first threshold, determine that the region has a leakage of a first gas,
        responsive to determining the second absorption rate above a second threshold, determine that the region has a leakage of a second gas, and
        trigger the image generator, in response to determining that the region has a leakage of the first gas and second gas, capture an image of the region of the pipeline in the range of wavelengths.

2. The system of claim 1, further comprising:
    a second light source to emit a third outgoing light beam having a third wavelength in an infrared range, the third outgoing light beam traversing the area between the system and the pipeline towards the region of the pipeline.

3. The system of claim 2, wherein:
    the third outgoing light beam is absorbed by the first gas leaked from the pipeline and the first gas absorbing the third outgoing light emits light having a fourth wavelength.

4. The system of claim 3, wherein the range of wavelengths does not include the first wavelength or the third wavelength.

5. The system of claim 3, wherein the controller is further configured to:
    determine the image includes information representing a leakage by analyzing pixel values of pixels of the image and a number of pixels having pixel values above a threshold.

6. The system of claim 1, wherein:
    the first outgoing light beam and the second outgoing light beam are multiplexed according to a timing pattern, and
    the controller is further configured to:
        de-multiplex the first incoming light beam and the second incoming light beam.

7. The system of claim 1, further comprising:
    a storage device to store the images.

8. The system of claim 1, further comprising:
    a communication module to provide the image to a user device.

9. A method for remotely detecting gas leakage from a pipeline comprising:
    emitting, from a first light source, a first outgoing light beam having a first wavelength in a mid-infrared (IR) range and a second outgoing light beam having a second wavelength in the mid-IR range;
    modulating the first outgoing light beam with a first modulation signal to generate a first modulated outgoing light beam, the first modulation signal having a first frequency;
    modulating the second outgoing light beam with a second modulation signal to generate a second modulated outgoing light beam, the second modulation signal having a second frequency different from the first frequency, the first modulated outgoing light beam and the second modulated outgoing light beam traversing towards a region of the pipeline;
    collecting, at a first light detector, a first incoming light beam having the first wavelength and a second incoming light beam having the second wavelength, the first incoming light beam being the first modulated outgoing light beam reflected off of an outer surface of the region and the second incoming light beam being the second modulated outgoing light beam reflected off of the outer surface of the region;
    comparing an intensity of the first incoming light beam to an intensity of the first outgoing beam to calculate a first absorption rate;
    comparing an intensity of the second incoming light beam to an intensity of the second outgoing beam to calculate a second absorption rate;
    responsive to determining the first absorption rate above a first threshold and the second absorption rate above a second threshold, determining that the region has a leakage of a first gas and the second gas; and
    triggering an image generator to capture an image of the region of the pipeline in response to determining that the region has the leakage of the first gas and the second gas.

10. The method of claim 9, further comprising:
    emitting, from a second light source, a third outgoing light beam having a third wavelength in an infrared range, the third outgoing light beam traversing the area between the system and the pipeline towards the region of the pipeline.

11. The method of claim 10, wherein:
    the third outgoing light beam is absorbed by the first gas leaked from the pipeline and the first gas absorbing the third outgoing light emits light having a fourth wavelength.

12. The method of claim 11, wherein the range of wavelengths does not include the first wavelength or the third wavelength.

13. The method of claim 11, further comprising:
    determining the image includes information representing a leakage by analyzing pixel values of pixels of the image and a number of pixels having pixel values above a threshold.

14. The method of claim 9, wherein:
the first modulated outgoing light beam and the second modulated outgoing light beam are multiplexed according to a timing pattern, and
the method further comprises:
de-multiplexing the first incoming light beam and the second incoming light beam.

15. The method of claim 9, further comprising:
storing the images on a storage device.

16. The method of claim 9, further comprising:
providing the image to a user device.

* * * * *